United States Patent [19]
Mikulicz et al.

[11] 3,957,902
[45] May 18, 1976

[54] ABSORPTION OF HYDROGEN FLUORIDE IN ALKYLATED HYDROCARBON PRODUCT

[75] Inventors: Michael Z. Mikulicz, Palatine; William G. Boney, Rolling Meadows; Bipin V. Vora, Buffalo Grove, all of Ill.

[73] Assignee: Universal Oil Products Company, Des Plaines, Ill.

[22] Filed: Nov. 4, 1974

[21] Appl. No.: 520,811

[52] U.S. Cl. ................................ 260/683.48
[51] Int. Cl.² ................................. C07C 3/54
[58] Field of Search .................. 260/683.48, 683.42

[56] References Cited
UNITED STATES PATENTS

| | | |
|---|---|---|
| 2,320,629 | 6/1943 | Matuszak ................. 260/683.42 |
| 2,379,368 | 6/1945 | Matuszak ................. 260/683.48 |
| 2,399,368 | 4/1946 | Matuszak ................. 260/683.48 |

*Primary Examiner*—Delbert E. Gantz
*Assistant Examiner*—G. J. Crasanakis
*Attorney, Agent, or Firm*—James R. Hoatson, Jr.; Robert W. Erickson; William H. Page, II

[57] ABSTRACT

Byproduct or waste gases, containing hydrogen fluoride, from an HF-catalyzed hydrocarbon alkylation process are contacted with a stream of liquid hydrocarbon essentially free from hydrogen fluoride. Hydrogen fluoride from the waste gases is absorbed within the liquid hydrocarbon and is returned to the process therewith. Resulting waste gases are of reduced hydrogen fluoride content, and the loss of hydrogen fluoride upon disposal of these gases is thereby reduced.

2 Claims, 2 Drawing Figures

ABSORPTION OF HYDROGEN FLUORIDE IN ALKYLATED HYDROCARBON PRODUCT

BACKGROUND OF THE INVENTION

1. Field of the Invention

The field of art to which this invention pertains in hydrocarbon processing. It particularly relates to the treatment of byproduct gases from hydrocarbon processing plants which utilize hydrogen fluoride as a catalyst.

2. Prior Art

The production of higher molecular weight isoparaffins, having valuable antiknock properties as motor fuel, is of considerable important in the petroleum refining industry. A convenient source of such higher molecular weight isoparaffins is the catalytic alklation of lower boiling isoparaffins, such as isobutane, with olefins such as propene, butenes, and amylenes. It is well known in the art that catalytic alkylation using hydrofluoric acid has become an important tool for preparing motor fuel blending components.

Hydrofluoric acid is a hazardous chemical with properties peculiar to itself which call for special handling and treatment. With improper treatment it can be lethal. For this reason processes for its use must be equipped with systems which effectively prevent its escape into the atmosphere. Common practice in the art is to provide a relief system which collects the effluent of all relief valves and other sources within the process from which hydrogen fluoride may be expected to be released. As is well known in the art, relief valves are commonly fitted to processing zones which may operate at superatmospheric pressures. These valves open and allow an exhaust of material from the process at pressure levels above normal but below that at which structural damage to the processing zones would occur. It is quite common during the cessation or initiation or operation of a process that processing zones are periodically over-pressured. During these periods of overpressure, the associated relief valves open and maintain safe pressure levels by exhausting material from the affected zones. The exhausts from relief valves pass to a relief system which, in current plant designs, carries the exhaust to a treating process wherein the HF contained within the exhaust is chemically altered and made safe for entry into normal waste disposal facilities.

It is common in the art to use a treating process wherein acidic gases from the relief system are countercurrently contacted with an aqueous solution of a metal hydroxide, such as potassium hydroxide, within an elaborate plate-type contact tower. Where KOH is used as the metal hydroxide to treat a gas containing HF the ensuing reaction may be represented by the equation:

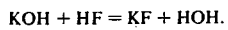

KOH + HF = KF + HOH.

The resulting aqueous KF solution is further contacted with Ca(OH)$_2$ to precipitate CaF$_2$ which is highly insoluble in water. The fluoride precipitate, in the form of a sludge, is then disposed of as waste.

Operators of these prior art processes must replenish the HF lost by chemical treatment of water gases. The disposal of a precipitate sludge also poses an inconvenience to the processor.

We have found that HF can be recovered from waste gases by the use of hydrocarbon streams already existing within the process. In this manner HF leaving the process in waste gases is not chemically altered but is returned to the process for further use. HF loss from the process and the HF replenishment which loss necessitates are greatly reduced. The use of elaborate and inconvenient prior art processes involving chemical treatment and disposal of treatment wastes is avoided by use of the present invention.

BRIEF SUMMARY OF THE INVENTION

Our invention involves a process for the recovery of hydrogen fluoride prior to disposal of waste HF alkylation process gases containing hydrogen fluoride. A hydrocarbon liquid selected to be essentially free of hydrogen fluoride contacts the waste gases, absorbs hydrogen fluoride and returns it to the process. Waste gases disposed of subsequent to this contact are of reduced HF content.

OBJECTS AND EMBODIMENTS

It is an object of this invention to remove hydrogen fluoride from normally vaporous hydrocarbon admixtures containing HF.

Still another object of our invention is to provide an HF-catalyzed hydrocarbon alkylation process with reduced HF loss.

In one embodiment our invention affords an improved, hydrogen fluoride-catalyzed process for the production of alkylated hydrocarbons from olefins and alkylatable hydrocarbons of the type in which the hydrogen fluoride contained in byproduct gases is chemically neutralized and discarded, wherein the improvement comprises (i) contacting the waste gases with a hydrogen-fluoride free, non-olefinic, liquid hydrocarbon stream selected from said process; (ii) absorbing within said liquid hydrocarbon stream at least a portion of said hydrogen fluoride within said waste gases; (iii) returning said liquid hydrocarbon stream, containing absorbed hydrogen fluoride, to said process.

BRIEF DESCRIPTION OF THE DRAWINGS

The attached drawings illustrate particular embodiments of the present invention. Only such details are included as are necessary for a clear understanding or our invention, and no intention is thereby made to unduly limit its scope. Certain items necessary to the operation of the process but unnecessary to its understanding, such as certain process streams, valves, pumps, instrumentation and other equipment have been omitted for the sake of clarity.

Referring now to FIG. 1, a first feed stream, comprising olefinic hydrocarbons, enters reaction zone 1 in conduit 5, and a second feed stream, comprising alkylatable hydrocarbons, enters reaction zone 1 in conduit 4.

Figure 1:
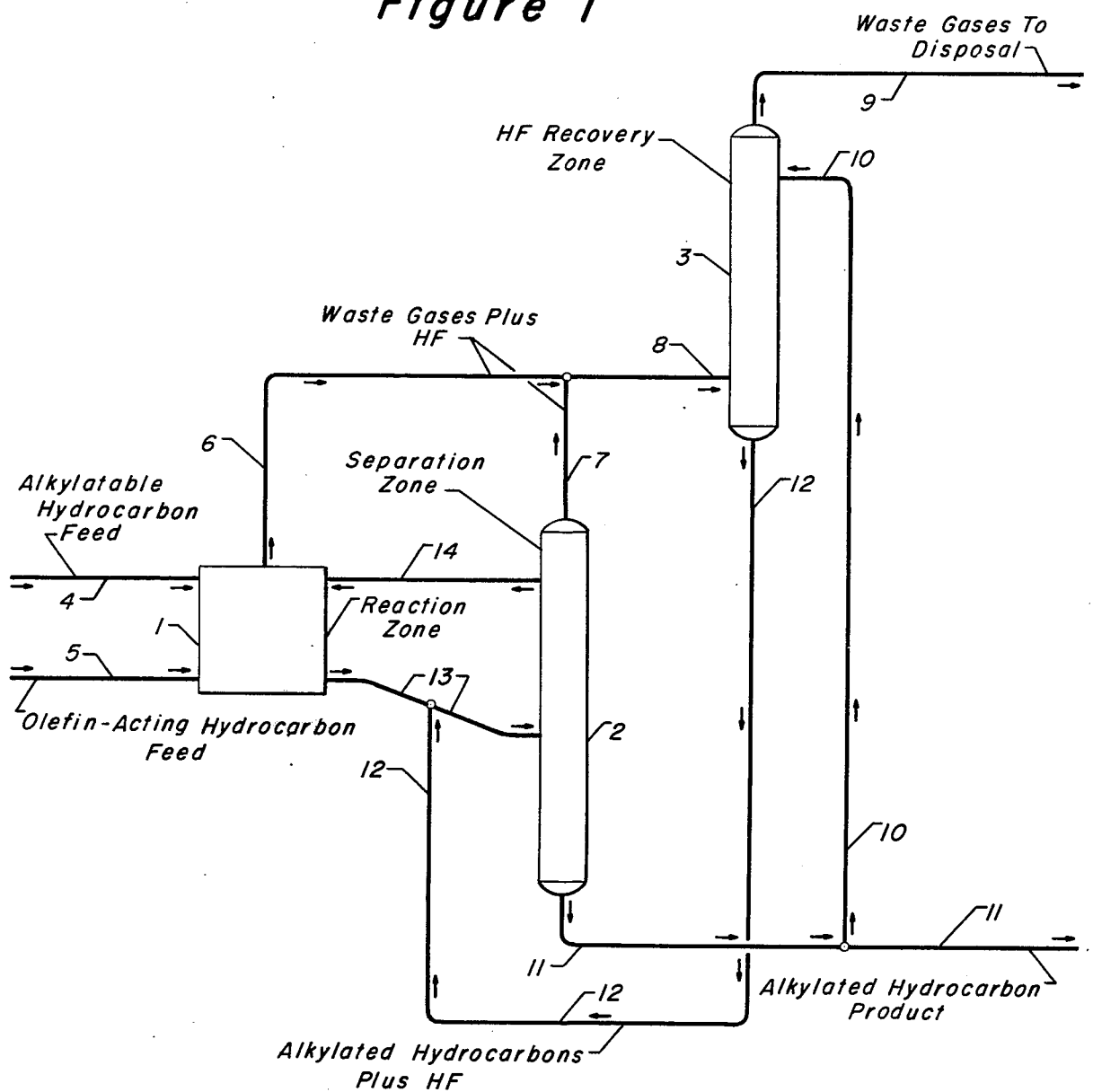
FIG. 1 is a schematic representation showing an HF alkylation process having reaction zone 1, separation zone 2 and HF recovery zone 3 in one embodimental configuration of the present invention.

A mixture of HF, alkylated hydrocarbons and unreated alkylatable hydrocarbons exits reaction zone 1 in conduit 13 and passes to separation zone 2 where an alkylated hydrocarbon product is separated from the mixture and exits separation zone 2 in conduit 11. HF and unreacted alkylatable hydrocarbons exit separation zone 2 in conduit 14 and return to the reaction zone.

Waste gases, containing HF, exit reaction zone 1 in conduit 6 and combine with similar waste gases exiting separation zone 2 in conduit 7. The combined waste gases pass to HF recovery zone 3 in conduit 8.

A portion of the alkylated hydrocarbon product exiting the separation zone in conduit 11 passes to HF recovery zone 3 in conduit 10. Alkylated hydrocarbons entering the HF recovery zone in conduit 10 absorb HF from the waste gas-HF mixture within the HF recovery zone. Alkylated hydrocarbons and absorbed HF exit the HF recovery zone in conduit 12 and pass to conduit 13 wherein they are conducted to separation zone 2. Waste gases, substantially free from HF, exit the HF recovery zone in conduit 9.

Figure 2:
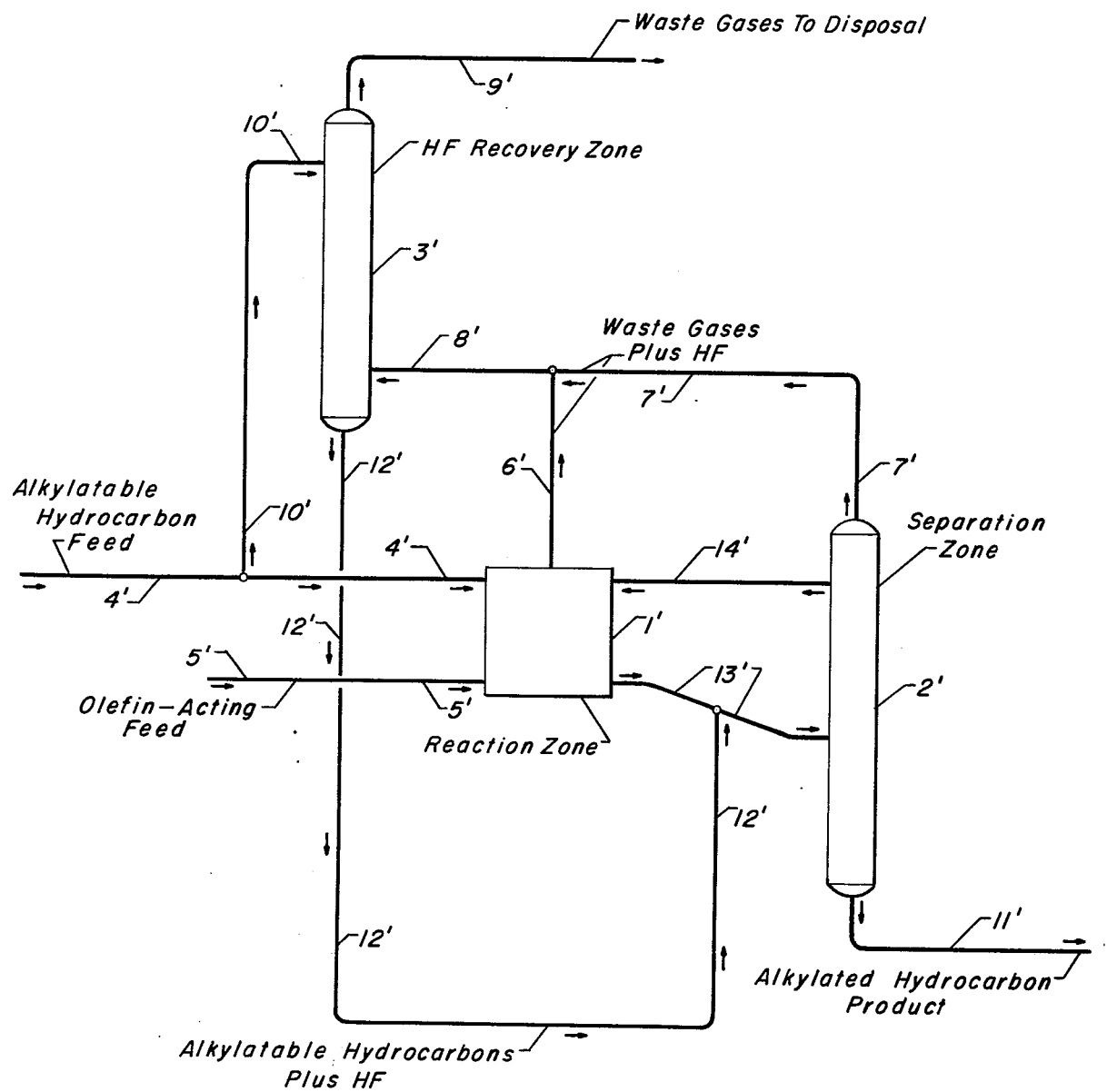
FIG. 2 is yet another configuration of our invention utilizing reaction, separation and HF recovery zones 1', 2' and 3', respectively.

Referring now to FIG. 2, a second embodiment is shown wherein a reaction zone feed stream is used, instead of an alkylated hydrocarbon product stream, to absorb HF in the HF recovery zone of this invention. A first feed stream, comprising olefinic hydrocarbons, enters reaction zone 1' in conduit 5°, and a second feed stream, comprising alkylatable hydrocarbons, enters reaction zone 1' in conduit 4'.

A mixture of HF, alkylated hydrocarbons and unreacted alkylatable hydrocarbons exits reaction zone 1' in conduit 13' and passes to separation zone 2' where an alkylated hydrocarbon product is separated from the mixture and exits separation zone 2' in conduit 11°. HF and unreacted alkylatable hydrocarbons exit separation zone 2' in conduit 14' and return to the reaction zone.

Waste gases, containing HF, exit reaction zone 1' in conduit 6' and combine with similar waste gases exiting separation zone 2' in conduit 7'. The combination waste gases pass to HF recovery zone 3' in conduit 8'.

A portion of said second feed stream in conduit 4', comprising alkylatable hydrocarbons, passes to HF recovery zone 3' in conduit 10'. Alkylatable hydrocarbons entering the HF recovery zone in conduit 10' absorb HF from the waste gas-HF mixture within the HF recovery zone. Alkylatable hydrocarbons and absorbed HF exit and HF recovery zone in conduit 12' and pass to conduit 13' wherein they are conducted to separation zone 2'. Waste gases, substantially free from HF, exit the HF recovery zone in conduit 9'.

DETAILED DESCRIPTION OF THE INVENTION

Hydrofluoric acid is particularly dangerous because of its effect upon all living body tissues. It is harmful in practically any concentration in either liquid or vapor form. In solution, hydrofluoric acid breaks down into hydrogen and fluorine which are present as what are known as hydrogen ions and fluorine ions. Hydrofluoric acid causes a surface burn to bodily tissues through the action of the hydrogen ions. In addition, the fluorine ions penetrate below the surface and continue to attack and destroy tissue and bone until they are precipitated as magnesium or calcium fluoride by the action of magnesium or calcium compounds present in the body or administered in medical treatments. The fluorine ions effect deep seated, ulcerous sores which commonly resist therapeutic efforts. The effect of the acid uon skin and mucus tissue is to cause extreme pain which often occurs only after the acid has been absorbed below the surface, such that washing is largely ineffective. This effect is commonly known to personnel of hydrogen fluoride processes as "delayed-action burn".

Because of the character of these acids it is essential that they not be released into the atmosphere. For this reason elaborate and costly systems are designed into process plants using HF to collect the exhaust of waste gases from the process and remove the HF from it before conduction to waste disposal facilities.

Byproduct, or waste, gases from hydrocarbon processes are comprised, primarily, of relief, vent and purge gases. Relief gases result from the opening of relief valves within the plant. When a relief valve associated with an acid-bearing processing zone opens, it exhausts acid gases into the relief system which conducts the gases to treating facilities for removal of acidic components. Vent and purge gases result, respectively, from the depressuring and cleansing of unit operations equipment, often in preparation for mechanical maintenance. The acidic materials remaining within a broken pump, for example, are vented and purged from the pump through special conduits which conduct the acidic materials and the purging medium to the relief system.

Traditional processes used for treatment of relief, vent and purge gases for removal of HF generally involve contact of the gases with a liquid treating medium and subsequent regeneration of the treaing medium. The resultant waste product, usually in the form of a precipitate sludge of a metal fluoride is inconvenient to handle and dispose. Common practice in the art is to use special vehicles, equipped with vacuum actuated retrieval systems, to aspirate the sludge into tanks for its translation to a place of disposal. The cost and complexity of operation of these prior art HF removal processes, combined with the irrecoverable loss of HF in the sludge which they produce, make them a source of bother and inconvenience to operators of HF alkylation process plants.

Our invention provides an HF alkylation process which is an advance over the prior art by virtue of the inclusion of a zone for recovery of HF from byproduct or waste gases.

Alkylatable hydrocarbons suitable for use in the process of our invention are paraffinic hydrocarbons having a tertiary carbon atom, such as 2-methylbutane, 2-methylpentane, isobutane and the like. Olefinic hydrocarbons which may be suitably used in our invention include $C_3$ to $C_{20}$ olefinic hydrocarbons. Hydrogen fluoride, HF, is used as the alkylation catalyst. A preferred alkylation catalyst contains sfrom 80–90% hydrogen fluoride, less than 2% water and soluble organic material as the remainder.

The process of our invention comprises a reaction zone, a separation zone and an HF recover zone. The reaction zone may be any of the designs well known in the art which provides for contact of the alkylatable hydrocarbon feed with the olefin feed and with HF alkylation catalyst. Alkylation conditions to be maintained within the reaction zone include a temperature of from about 0°F to about 150°F, and a pressure of about 1 atmosphere to about 40 atmospheres. A preferred range of temperature is from about 30°F to about 100°F.

The separation zone of the process receives a reaction product stream from the reaction zone and separates it into an alkylated hydrocarbon product and one or more recycle streams which are returned to the reaction zone for further participation therein. The recycle stream or streams comprise unreacted alkylatable hydrocarbons and HF.

A characteristic of HF alkylation plants is that they produce waste gases from their processing zones. Waste gases from the reaction zone and the separation zones of the process of our invention pass to the HF recovery zone where HF, a soluble component of the waste gas mixture, is dissolved in a liquid. The liquid used may be a non-olefinic, HF-free hydrocarbon stream selected from the alkylation process. We prefer to use either a portion of the alkylatable hydrocarbon feed or a portion of the alkylated hydrocarbon product. This liquid is returned to the separation zone after absorption of HF in the HF recovery zone.

The HF recovery zone may be a tower filled with solid packing material, a tower containing a number of sieve or bubble-cap plates, or an empty tower into which liquid is sprayed. Selection of the type and size of tower used depends upon the individual plant, according to the projected or actual waste gas rate and composition, and is well within the technical abilities of those skilled in the art. A preferred configuration provides countercurrent flows of liquid and waste gas within the HF recovery zone.

The operating conditions which may be used in the HF recovery zone of the process of our invention include a temperature of from about 35°F to about 200°F and a pressure of from about 0 psig to about 500 psig. Preferred temperatures are those lowest in the acceptable range. Pressure is preferrably maintained as high as possible within the acceptable range.

Sufficient contact between liquid and waste gas within the HF recovery zone is provided such that waste gas exiting the HF recovery zone is essentially HF-free.

In one embodiment of our invention 6,300 barrels per stream day of a mixture of olefin and isoparaffin feeds enter the reaction zone. A mixture composed of the two feeds would be of approximately the following composition, expressed in mole percent: propene, 16.9; propane, 8.7; butene, 25.2; isobutane, 43.9; normal butane, 5.3.

Waste gases from all processing zones enter the HF recovery zone where they contact 2366 barrels per stream day of alkylated hydrocarbons withdrawn from the separation zone. Waste gases leaving the HF recovery zone are of sufficiently reduced HF content to enable them to be disposed of by burning in the atmosphere. The conditions within the HF recovery zone are a pressure of 5 psig and a temperature of 100°F. The net production of alkylated hydrocarbons is 4732 barrels per stream day.

In another embodiment of our invention 7,272 barrels per stream day of isoparaffin and olefin feeds enter the reaction zone. A mixture of these two feeds would be of approximately the following composition, expressed in mole percent: propene, 20.0; propane, 8.6; butene, 23.7; isobutane, 42.2; normal butane, 5.5. 7510 barrels per stream day of alkylated hydrocarbons exit the separation zone. 2000 barrels per stream day of the alkylated hydrocarbons are passed to the HF recovery zone for contact with waste gases, and 5272 barrels per stream day are withdrawn as a net product of alkylated hydrocarbons. Waste gases, having contacted the 2000 barrels per stream day of alkylated hydrocarbons are essentially HF-free. Operating conditions within the HF recovery zone are a pressure of 25 psig and a temperature of 110°F. The 2000 barrels per stream day of alkylated hydrocarbons plus absorbed HF return from the HF recovery zone to the separation zone of the process.

We claim as our invention:

1. In an alkylation process wherein an olefin and an alkylatable hydrocarbon are contacted with hydrogen fluoride in a reaction zone and wherein waste gases containing HF are collected from said process; the improvement comprising:
    a. separating the alkylation reaction mixture from said reaction zone into an alkylated hydrocarbon product, a stream of unreacted alkylatable hydrocarbon and hydrogen fluoride, and a gaseous stream comprising hydrogen fluoride;
    b. returning said stream of unreacted alkylatable hydrocarbon and hydrogen fluoride to said reaction zone;
    c. contacting said waste gases containing HF and said gaseous stream with a first portion of said alkylated hydrocarbon product to absorb hydrogen fluoride in said product;
    d. separating waste gases substantially reduced in HF from said contacting step (c)
    e. passing said alkylated product containing absorbed hydrogen fluoride from contacting step (c) to separating step (a), and
    f. recovering a second portion of said alkylated hydrocarbon product from said process.

2. An alkylation process which comprises the steps of:
    a. reacting an olefin with an alkylatable hydrocarbon in contact with hydrogen fluoride catalyst in a reaction zone;
    b. removing from the reaction zone a gaseous stream containing hydrogen fluoride;
    c. supplying the remainder of the alkylation reaction mixture from said zone to a separating zone and therein separating said remainder of the reaction mixture into an alkylated hydrocarbon product, a stream of unreacted alkylatable hydrocarbon and hydrogen fluoride, and a gaseous stream comprising hydrogen fluoride;
    d. returning said stream of unreacted alkylatable hydrocarbon and hydrogen fluoride to said reaction zone;
    e. commingling the gaseous stream from separating step (c) with the gaseous stream from step (b) and contacting the resultant mixture with a first portion of said alkylated hydrocarbon product to absorb hydrogen fluoride from the gaseous streams in said portion of the product;
    f. supplying resultant HF-containing alkylated product to separating step (c); and
    g. recovering a second portion of said alkylated hydrocarbon product from said process.

* * * * *